United States Patent
Tan et al.

(10) Patent No.: US 9,918,630 B2
(45) Date of Patent: Mar. 20, 2018

(54) SYSTEMS AND METHODS OF GLAUCOMA DIAGNOSIS BASED ON FREQUENCY ANALYSIS OF INNER RETINAL SURFACE PROFILE MEASURED BY OPTICAL COHERENCE TOMOGRAPHY

(71) Applicants: Ou Tan, Portland, OR (US); David Huang, Portland, OR (US)

(72) Inventors: Ou Tan, Portland, OR (US); David Huang, Portland, OR (US)

( * ) Notice: Subject to any disclaimer, the term of this patent is extended or adjusted under 35 U.S.C. 154(b) by 0 days.

(21) Appl. No.: 15/253,597

(22) Filed: Aug. 31, 2016

(65) Prior Publication Data
US 2017/0055829 A1   Mar. 2, 2017

Related U.S. Application Data

(60) Provisional application No. 62/213,072, filed on Sep. 1, 2015.

(51) Int. Cl.
| | | |
|---|---|---|
| *A61B 3/12* | (2006.01) | |
| *A61B 3/00* | (2006.01) | |
| *A61B 3/10* | (2006.01) | |

(52) U.S. Cl.
CPC .......... *A61B 3/1225* (2013.01); *A61B 3/0025* (2013.01); *A61B 3/102* (2013.01); *G06T 2207/30041* (2013.01)

(58) Field of Classification Search
CPC ......... A61B 3/102; A61B 3/14; A61B 5/0066; A61B 3/13; A61B 3/12
USPC .................................................. 351/206, 246
See application file for complete search history.

(56) References Cited

U.S. PATENT DOCUMENTS

| | | |
|---|---|---|
| 5,233,517 A | 8/1993 | Jindra |
| 8,474,978 B2 | 7/2013 | Huang et al. |
| 2011/0228223 A1 | 9/2011 | Jiao et al. |
| 2013/0182895 A1 | 7/2013 | Touzov et al. |
| 2013/0271757 A1 | 10/2013 | Kang et al. |
| 2013/0281841 A1 | 10/2013 | Everett el al. |
| 2015/0116664 A1* | 4/2015 | Uchida ................ A61B 3/0025 351/206 |

FOREIGN PATENT DOCUMENTS

NO       2015-103566 A2      7/2015

OTHER PUBLICATIONS

International Appln. No. PCT/US2016/049758, Int. Search Report and Written Opinion, dated Dec. 8, 2016.
HATCH et al.—Laser scanning tomography of the optic nerve head in ocular hypertension and glaucoma, Brit. J. Ophthalmology Oct. 9, 1997, pp. 871-876.
Jia et al., Quantitative optical coherence tomography angiography of vascular abnormalities in the living human eye, Proc. Nat. Acad. Sci. USA, Apr. 20, 2015, pp. E2395-E2402.

(Continued)

*Primary Examiner* — Hung Dang

(57) ABSTRACT

A method for detecting glaucoma in a subject based on spatial frequency analysis of the inner limiting membrane (ILM) as obtained from optical coherence tomography (OCT) image data is disclosed. Based on the spatial frequency content of the analyzed ILM profile, a quantity called the Retinal surface contour variability (RSCV) is calculated and the presence or absence of a glaucoma condition is determined based on the RSCV magnitude.

15 Claims, 12 Drawing Sheets

(56) References Cited

OTHER PUBLICATIONS

Kim et al., Additive Diagnostic Role of Imaging in Glaucoma: Optical Coherence Tomography and Retinal Nerve Fiber Layer Photography, Investigative Ophthalm. Vis. Sci., vol. 55, No. 12, pp.8024-8030, Dec. 2014.
LIU et al., Optical Coherence Tomography Angiography of the Peripapillary Retina in Glaucoma, JAMA Ophthalm. Sep. 2015; 133(9), pp. 1045-1052.
LOEWEN et al., Combining measurements from three anatomical areas for glaucoma diagnosis using Fourier-domain optical coherence tomography, Brit. J. Ophthalm., 2015, 99, 1224-1229.
Moreno-Montes et al., Comparison of Retinal Nerve Fiber Layer Thickness Values Using Stratus Optical Coherence Tomography and Heidelberg Retina Tomograph-III, J. Glaucoma, vol. 18, No. 7, Sep. 2009, pp. 528-534.
Tan et al.., Detection of Macular Ganglion Cell Loss in Glaucoma by Fourier-Domain Optical Coherence Tomography, Ophthalmology, vol. 116, No. 12, Dec. 2009, pp. 2305-2314.
Tan et al., Mapping of Macular Substructures with Optical Coherence Tomography for Glaucoma Diagnosis, Ophthalmology, vol. 115, No. 6, Jun. 2008, pp. 949-956.

\* cited by examiner

SYSTEMS AND METHODS OF GLAUCOMA DIAGNOSIS BASED ON FREQUENCY ANALYSIS OF INNER RETINAL SURFACE PROFILE MEASURED BY OPTICAL COHERENCE TOMOGRAPHY

ACKNOWLEDGEMENT OF GOVERNMENT SUPPORT

This invention was made with the support of the United States government under the terms of Grant Numbers RO1 EY013516 and RO1 EY023285 awarded by the National Institutes of Health. The United States government has certain rights in this invention

FIELD

Generally, the field involves methods of using optical coherence tomography (OCT) in glaucoma detection. More specifically, the field involves methods of processing OCT datasets to characterize spatial variations along the inner retinal surface that are indicative of early glaucoma.

BACKGROUND

Glaucoma is a disease of the eye characterized by a loss of retinal ganglion cells and concomitant localized thinning of retinal tissue which can cause progressive, irreversible vision loss. Because of the irreversible nature of glaucomatous damage, early diagnosis and treatment are important for maintaining visual function. Optical coherence tomography (OCT) is a noninvasive, high resolution, depth-resolved volumetric imaging technique that is commonly used to visualize the cross-sectional morphology of the retina. OCT is currently used in glaucoma detection to measure the thickness of retinal nerve fiber layer (NFL) and ganglion cell complex (GCC). However, because overall and regional thickness of the retina and retinal layers is highly variable in the normal population, these structural parameters have low sensitivity to detect early morphological changes that may be associated with glaucoma. Moreover, segmentation of these structures requires sophisticated image processing techniques to reproducibly extract thickness measurements of different retinal layers. Thus a more sensitive approach for characterizing structural changes in the retina is needed.

SUMMARY

Disclosed herein are methods of measurement for use in OCT based on spatial frequency analysis of the inner limiting membrane (ILM). These methods, termed transverse spatial frequency analysis, can be used to detect focal changes in NFL morphology that are sensitive indicators of early glaucoma. In an embodiment of the transverse spatial frequency analysis method disclosed herein, the ILM is segmented from an OCT scan and expressed as an ILM elevation profile denoting ILM elevation as a function of transverse position. The OCT scan from which the ILM elevation profile is generated will typically be circular and centered about the optic nerve head, but such a circular scan path is not strictly required. In addition, instead of using a single ILM elevation profile (i.e., a one-dimensional curve) for the analysis described herein, multiple concentric ILW elevation profile scans may be combined such that together they comprise an ILM elevation profile that is a surface (i.e., a two-dimensional surface parameterized in the transverse and radial directions).

In the methods disclosed herein, the ILM elevation profile is characterized using spatial frequency analysis techniques to quantify the influence of surface variations along ILM. Compared to approaches which directly measure thickness variations within the retina, spatial frequency analysis of the ILM elevation profile is more easily implemented and reliably automated, as only a single anatomical structure—the ILM—needs to be segmented from the OCT scan. Moreover, spatial frequency analysis of ILM contour shows better sensitivity in differentiating normal and glaucomatous eyes based on structural features than approaches which directly measure thickness.

To simplify the presentation of spatial frequency data and facilitate the identification of glaucomatous profiles versus normal profiles, a metric called the "Retinal surface contour variability" (RSCV) is defined. The RSCV is calculated using specific frequency bands from the spatial frequency analysis which are associated with structural features that differentiate pathologic ILM elevation profiles from normal ones. In the case of glaucoma, the ILM elevation profile is differentiated by the presence of vessels protruding anteriorly from the retina and by depressions where NFL thinning has occurred. These focal variations in surface contour—localized protrusions and depressions—are not affected by the statistical variability in NFL thickness observed in the normal population; therefore these features are well-suited to the accurate detection of early glaucomatous NFL damage compared to less sensitive NFL thickness-based measures. Focal depressions and elevations are each associated with certain frequency bands in the spatial frequency spectrum of the contour profile and, as such, their contribution to the frequency content of the ILM elevation profile can be used in the calculation of RSCV to characterize glaucomatous damage. Furthermore, as these focal variations become more numerous and pronounced with glaucomatous progression, the RSCV index provides a measure of disease progression and severity.

The optimized frequency bands for use in characterizing a given optic neuropathy can be identified by performing spatial frequency analysis of the ILM elevation profiles for population of eyes already diagnosed with the neuropathy along with analysis of a population of normal eyes. Once identified, these frequency bands can be incorporated into a calculation of RSCV which, when compared to a population-derived threshold value, may indicate risk for a given optic neuropathy such as glaucoma. Examples of such a population comparison are presented below for a group of glaucomatous and normal eyes.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the embodiments disclosed herein are not limited to implementations that address any or all disadvantages noted in any part of this disclosure.

DETAILED DESCRIPTION

Figure 1:
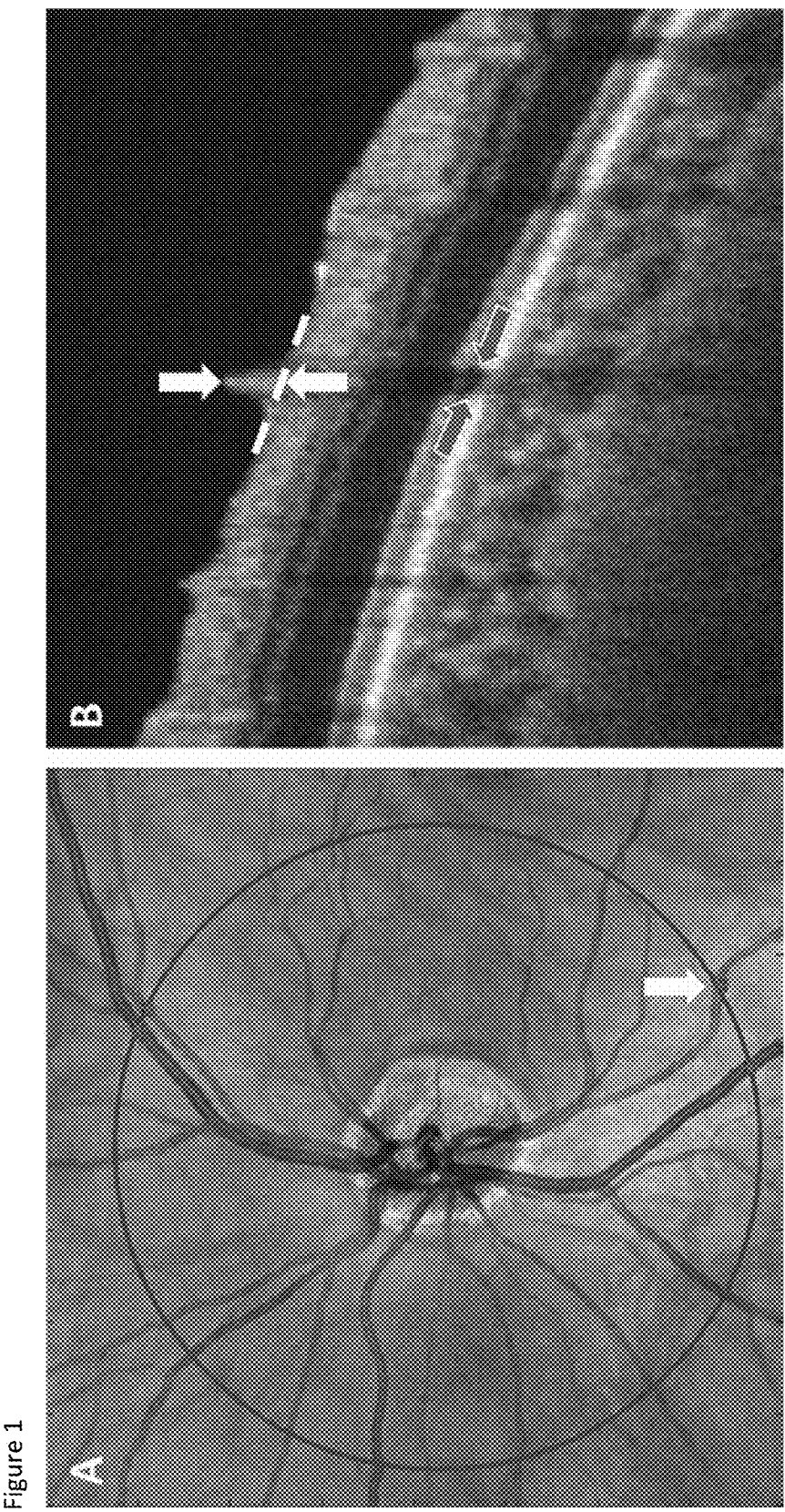
FIG. 1 is a panel of two images showing an exemplary sampling scheme for measuring retinal vessel relief height about the peripapillary region of the optic nerve head using optical coherence tomography (OCT). (A) En face OCT image from a volumetric OCT scan. A circular scan was resampled from the volumetric scan. The transverse position of the circular scan is depicted by a blue circle. The vessel marked by the white arrow is depicted in (B), as part of a representative cross-sectional scan of a major retinal vessel and underlying retina. The vessel relief height is depicted between the white arrows, the retinal plane is depicted by a dashed line, and a shadowgraphic projection artifact is depicted by the red arrows.

The following detailed description is directed to detecting optic neuropathy (for example, glaucoma) in a subject based on an analysis of the elevation profile of the inner limiting membrane of the retina using measurements obtained from optical coherence tomography image data. In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure information of a sample can be obtained using OCT imaging based on the detection of spectral interference. Such imaging can be two-dimensional (2-D) or three-dimensional (3-D), depending on the application. Structural imaging can be of an extended depth range relative to prior art methods and can be performed in real time. OCT imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

Optical coherence tomography (OCT) is a non-contact, non-invasive imaging modality for high-resolution, depth-resolved, cross-sectional, and three-dimensional (3D) imaging of biological tissue. Among its many applications, OCT has found widespread clinical use in ocular imaging and can be performed quickly and easily with minimal expertise. As an example, OCT image data may be used to measure retinal nerve fiber layer changes and ganglion cell complex loss to assist in detecting and diagnosing optic neuropathic diseases such as glaucoma.

The inner limiting membrane (ILM) defines the inner boundary of the retinal NFL and is the boundary separating the retina from the vitreous body in the eye. In OCT images the ILM has high contrast with the clear vitreous media at the vitreous interface and is thus easily segmented. When viewed in cross section, the surface of the ILM in healthy eyes is relatively smooth with intermittent small elevations at locations corresponding to underlying blood vessels. In OCT scans of glaucomatous eyes, however, it has been observed that the elevations on the ILM near surface vessels are more pronounced than in normal eyes indicating protrusion of vessels anteriorly. This anterior protrusion of vessel structure into the ILM has been described as "vessel relief," where the vessels are raised relative to the background ILM surface (see FIG. 1 and FIG. 5). In addition to vessel relief, the ILM surface of glaucomatous eyes is characterized by small depressions at sites where NFL bundle loss has occurred. These depressions reflect localized NFL thinning (i.e., reduced NFL thickness), one of the characteristic focal defects observed in glaucoma.

As shown in FIG. 1, it is possible to calculate a so-called "vessel relief height" (VRH) from a cross sectional scan OCT passing through such vessels to quantify the extent of their protrusion above the retinal plane. Similarly, it is possible to characterize focal thinning in the retina by measuring NFL thickness. Each of these approaches requires complex image processing and feature extraction techniques which may not always reliable or accurate. Furthermore, these approaches do not have adequate sensitivity to detect early changes in feature height or thickness that may be associated with glaucoma.

An alternative approach for identifying glaucomatous eyes, as disclosed herein, is to directly characterize the profile of ILM boundary in a way that the influence of 'bumps and depressions' on the ILM shape is captured. In the invention disclosed herein, a method for analyzing the ILM profile using spatial frequency analysis techniques is presented. This approach first entails extraction of a transverse section from a volumetric OCT so that a cross sectional image of the ILM is visualized. In typical embodiments, this transverse section will be in the shape of circle centered at the optic disc, but a transverse section in the shape of any simple closed curve such as an oval, an ellipse, or other non-self-intersecting continuous loop may be used. Non-closed curves may also be employed, as desired. Furthermore, in practice, the method described herein need not be limited a single transverse section to define the ILM boundary. Rather, multiple concentric, contiguous transverse sections may be used to capture the ILM boundary as a 2-D surface which can be analyzed for spatial frequency content. In embodiments, transverse sectional images can be generating by resampling and interpolating data from volumetric OCT scan datasets, but can also be acquired directly during an OCT imaging session by specifying a desired scan path (e.g., circular) for OCT systems having such capabilities. Further, in embodiments, it may be desirable to acquire multiple OCT scans for characterization of the ILM, for example, so that averaging can be applied to reduce motion artifacts.

The ILM boundary is then segmented from the transverse section image to generate an ILM elevation profile. In embodiments, this segmentation of the ILM boundary can be automated in a robust manner due to the high contrast between the ILM and the adjacent clear vitreous media. The resultant "ILM elevation profile" is then analyzed for spatial frequency content using a method such as the Fourier transform, wavelet analysis, discrete cosine transform, or other spectral analysis technique. In the case where the ILM elevation profile constitutes a surface representation, the spatial frequency analysis is conducted using the appropriate two-dimensional formulation.

In the spatial frequency domain, features such as vessel relief and NFL depression are captured in a specific range of transverse spatial frequencies; hence these specific frequency bands contain spectral information that can discriminate normal ILM profiles from those that are glaucomatous or have other optic neuropathies. Analysis of the frequency content of the ILM boundary that vessel size and vessel relief resides in the in middle-high frequency part of the spectrum and that NFL depressions correspond to a low frequency part of the spectrum. Thus the spectral power contained in specifically identified and optimized bands can be used to separate normal subjects from those and having glaucoma or other optic neuropathies that disrupt the ILM profile. The concept of Fourier analysis of a waveform representing the "hills and valleys" of digitized eye fundus photographs is described in U.S. Pat. No. 5,233,517 (incorporated by reference herein), but in that application the representation of topography of the retinal NFL is derived from low resolution gray-level densitometry values rather than cross sectional OCT images having actual depth information at high resolution.

A diagnostic index for glaucoma or other optic neuropathies called the RSCV is disclosed herein to characterize the frequency content that distinguishes pathologic profiles from normal profiles. This index is calculated using the amplitude or power spectrum within the specifically identified and optimized frequency band (or bands) from a spatial frequency analysis of the ILM profile. In various embodiments, the RSCV can be calculated using the mean amplitude within the frequency band(s), a weighted average of specific frequencies within the frequency band(s), power within the frequency band(s), or other formulations which highlight the features of interest. In embodiments, the frequency band(s) used to calculate RSCV can vary depending on the radius at which the transverse section data is acquired. In addition, the amplitudes associated with the frequency spectra and frequency bands can be scaled or otherwise transformed to facilitate data analysis. For example, logarithmic scaling of amplitudes in the frequency band(s) can be applied. In the case of glaucoma, the RSCV is formulated so that the relative depressions and the relief of blood vessels along the ILM are captured in the magnitude of RSCV index, reflecting the degree to which these features are present (e.g., the severity of the ILM profile non-smoothness). In embodiments, the RSCV index can be compared to a predetermined threshold value to indicate the presence or absence of a glaucoma condition.

EXAMPLES

The examples discussed below describe pilot studies of OCT measurements of the inner limiting membrane (ILM) of the retina surface in eyes of control participants and in participants with glaucoma, including patients further classified as having preperimetric glaucoma (PPG) and perimetric glaucoma (PG). These studies demonstrate the use of spatial frequency analysis of the ILM profile in detecting the presence or absence of an optic neuropathic disease such a glaucoma, in accordance with various embodiments. In these examples, OCT image data were obtained from circular transverse sections extracted from volumetric OCT scans, processing was performed on the OCT data, and parameters such as the retinal surface contour variability (RSCV), vessel relief height, and retinal nerve fiber layer (NFL) thickness were measured from the OCT data and used to detect the presence or absence of glaucoma. Embodiments may vary as to the methods of obtaining OCT image data, performing OCT data processing (e.g., using various conventional image processing techniques), and extracting parameters from the OCT data. For example, different embodiments may utilize different types of OCT, speeds of OCT, scan patterns (e.g., circular or non-circular scans), eye motion correction techniques, and/or frame averaging techniques. Further, though the examples illustrate applications of OCT technology to glaucoma detection, such an approach may be used for the detection of other optic neuropathic diseases or ocular disorders. For example, diseases that cause retinal NFL damage may also cause vessel relief distortion or introduce other variations in the shape of the ILM profile, and RSVC measurements may detect or assist in detecting these diseases. The examples discussed below are for illustrative purposes and are not intended to be limiting.

Example 1

Preliminary Study

Figure 2:
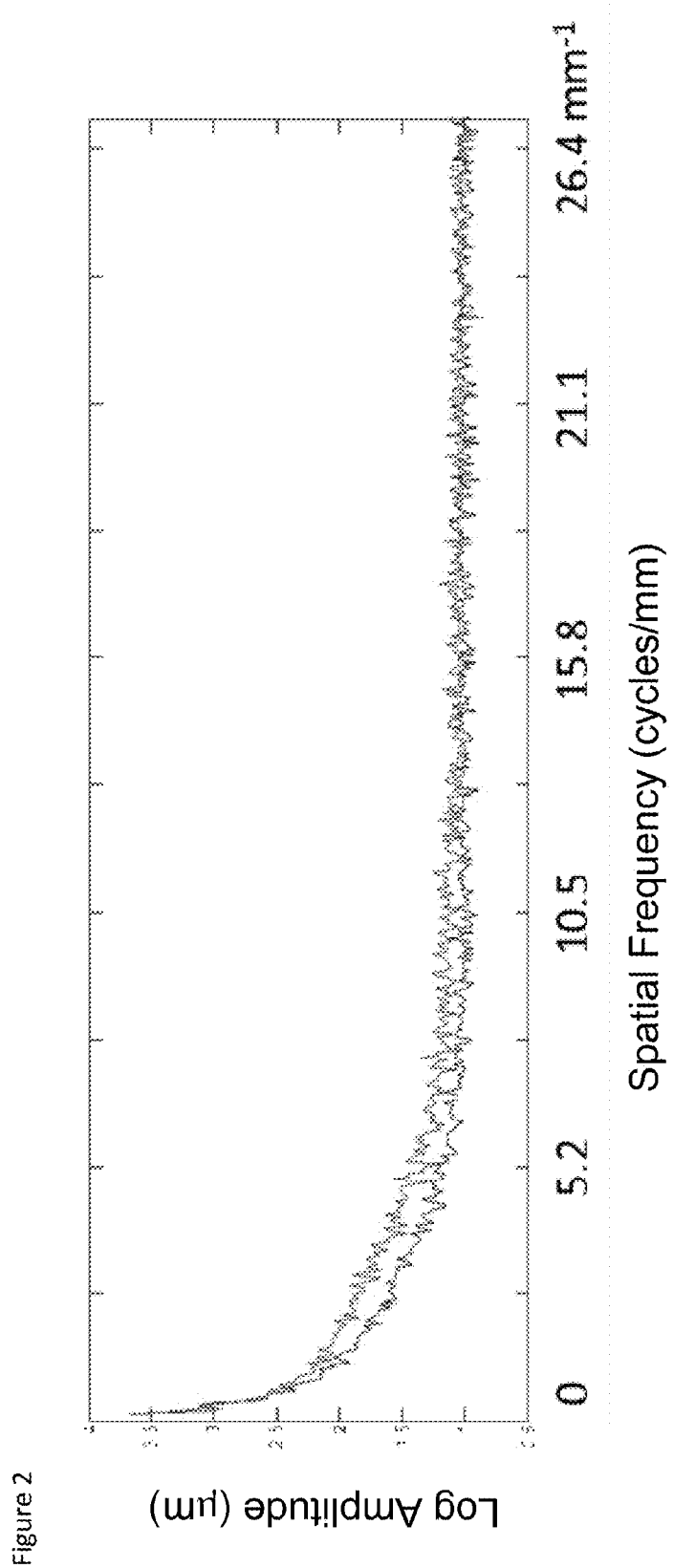
FIG. 2 is an exemplary graph showing the spectral content of the circumferential ILM profile for a normal group and a glaucoma group. The transverse spatial spectrum was calculated from the circumferential ILM profile at a radius of 3 mm. The average from the glaucoma group (red line, N=17) show increased spectral power in the middle spatial frequency range compared to the normal group (blue line, N=25).

Determination of Optimal Spatial Frequency Bands for Separating Normal and Glaucomatous Eyes OCT scans of 25 normal eyes and 17 glaucomatous eyes were analyzed to determine a range of transverse spatial frequencies over which the normal and glaucoma groups could be distinguished. Beginning with a given volumetric OCT dataset, a circular scan of radius 3 mm centered at the optic nerve head was resampled from the dataset to extract a cylindrical B-scan cross sectional image as depicted in FIG. 1. The inner limiting membrane (ILM) was detected on this cross sectional image and the expression of its height versus transverse (circumferential) position was termed the "ILM elevation profile." The frequency spectrum of the ILM elevation profile was determined using a Fourier transformation. Frequency spectra for the 25 normal eyes were averaged to produce a group average normal frequency spectrum. Similarly, the frequency spectra of the 17 glaucomatous eyes were averaged to produce a group average glaucoma frequency spectrum. These average normal and glaucomatous frequency spectra are shown in FIG. 2. Comparison of the these spectra reveals a non-overlapping region in a low frequency range of [0.2 cycle/mm~0.3 cycle/mm] and a middle frequency range of [0.7 cycle/mm~13.2 cycle/mm]; these frequency bands were deemed the optimized ranges for use in spectral analysis of ILM elevation profiles obtained from a circular scans with radius 3 mm in the example presented herein. Note that a frequency of 13.2 cycle/mm corresponds to 75 microns, which is in the range of a typical arteriole vessel size in the retina.

Figure 3:
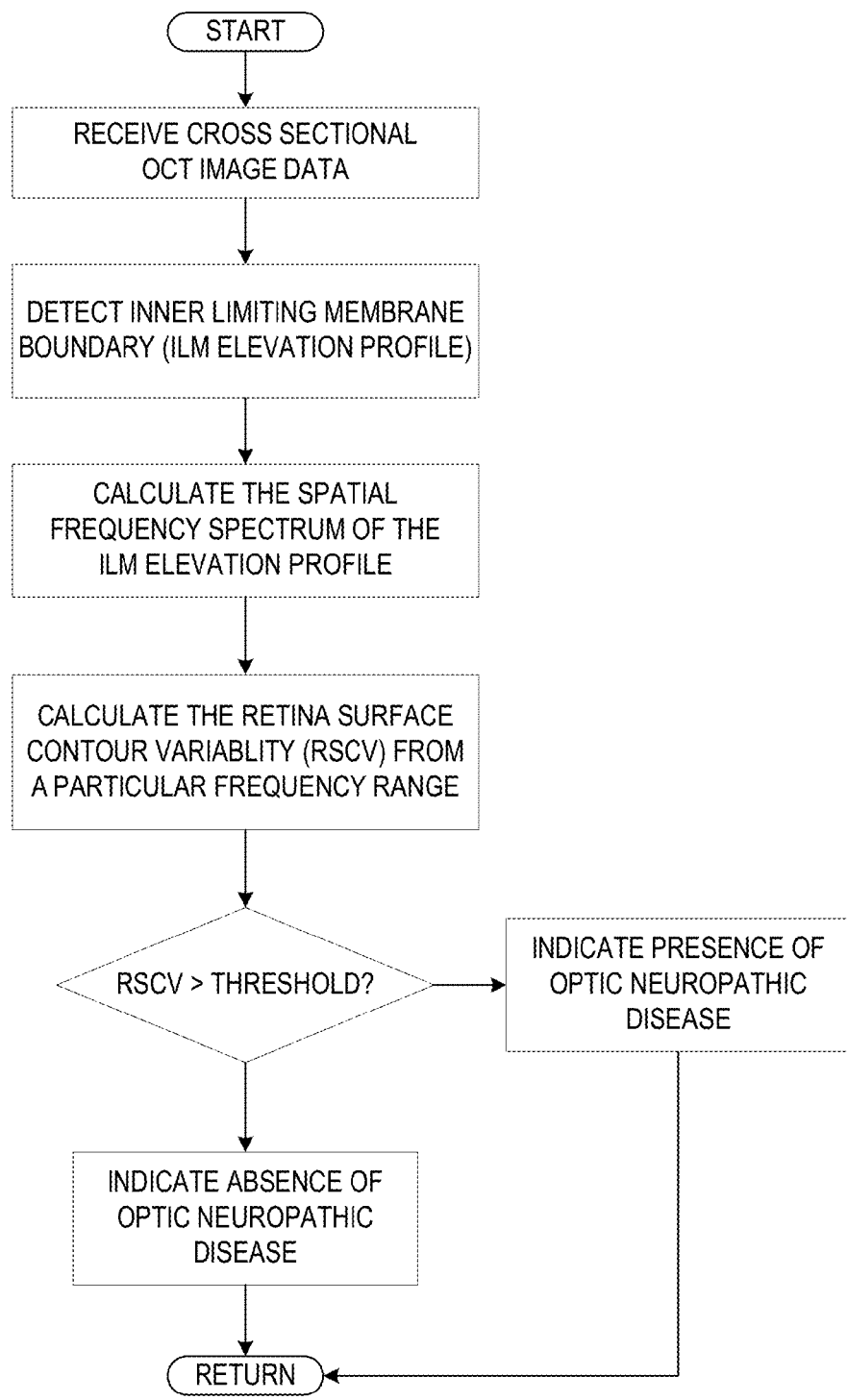
FIG. 3 is an exemplary flow chart for the calculation of retinal surface contour variability (RSCV) of an ILM profile and the comparison of that RSCV value to a predetermined threshold to indicate the presence or absence of an optic neuropathic disease.

An automatic algorithm to calculate the power in the optimized spatial frequency range of a subject's ILM elevation profile was developed. For this Example, RSCV was calculated as the average amplitude in the aforementioned optimized frequency bands. FIG. 3 shows a flowchart outlining an exemplary method for calculating RSCV from an OCT dataset for a subject and indicating whether that subject has an optic neuropathy based on the magnitude of the calculated RSCV value. It will be recognized by those skilled in the art that such an approach may be used to characterize RSCV for a population of normal and pathologic eyes to establish threshold RSCV values that are indicative of glaucoma or other optic neuropathies.
Comparison of Structural and Functional Measures of Glaucoma RSCV was compared to VRH, NFL thickness, and visual field mean deviation to test its diagnostic accuracy in detecting glaucoma. The three structural parameters RSCV, NFL thickness, and VRH were calculated using the same OCT datasets. RSCV and VRH were measured using a resampling radius of 3 mm. The radius of 3 mm was used because the inventors noted that this distance gives a robust measurement of VRH, but in embodiments other values of radius can be used (see Example 2 below). RSCV was calculated by mean-averaging the spatial frequency amplitudes within the optimized frequency bands separating glaucomatous from normal profile spectra. For VRH calculation, vessels were detected based on the intensity of the shadow cast on the retinal pigment epithelium (RPE) band. An average VRH value was calculated for vessels with diameter larger than 50 microns. NFL thickness was measured using a resampled circular scan with radius 1.7 mm. The diagnostic power of each of the parameters was evaluated by calculating area under the receiver operating characteristic curve (AROC). A visual field test was performed in a group of patients with early and moderate glaucoma to provide a functional measure of glaucoma. The visual field mean deviation (VFMD) from these tests was compared to RSCV to assess correlation.

Results

RSCV showed the highest AROC among the three structural parameters and the lowest standard error of the mean (See Table 1.). RSCV had marginally significantly higher AROC than average VRH (p=0.10). The combination of NFL and RSCV had a marginally significantly higher AROC (0.91, p=0.10) than NFL alone.

Figure 4:
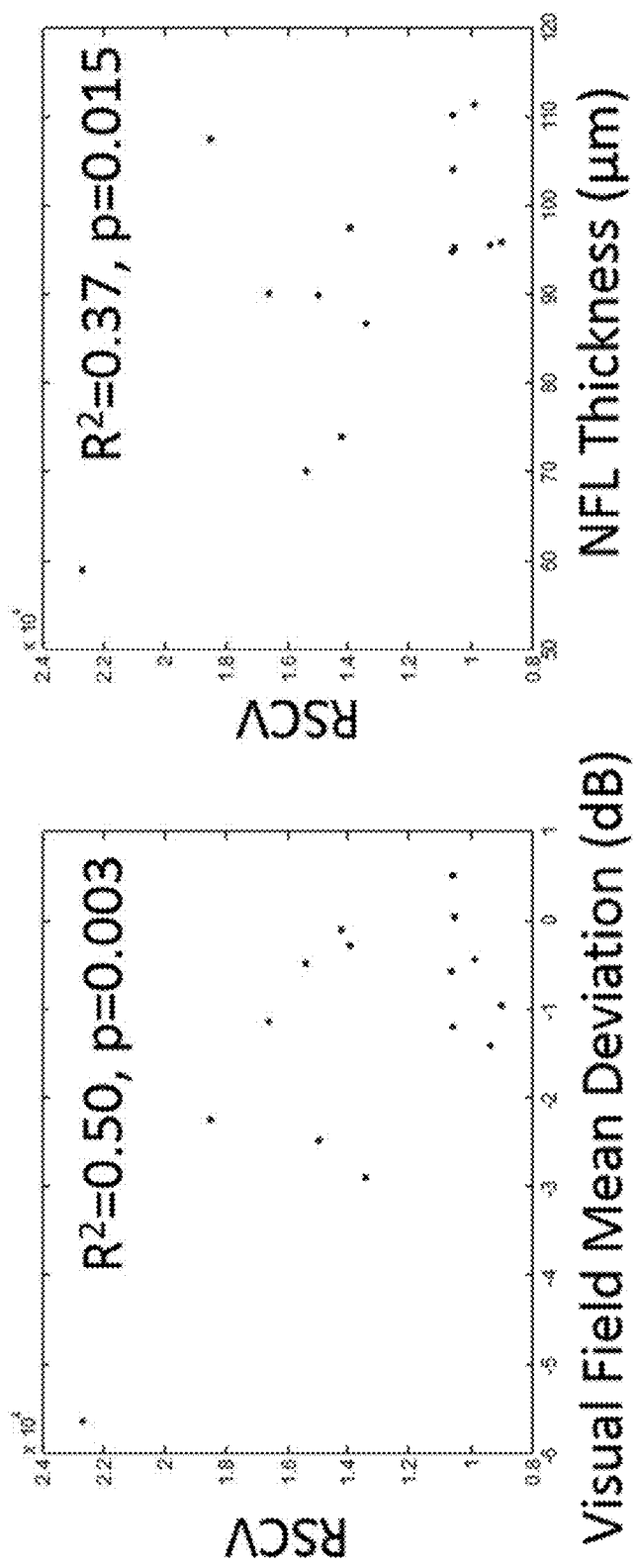
FIG. 4 is a panel of two graphs showing the relationship of RSCV to visual mean field deviation (MD) and to nerve fiber layer thickness (NFL thickness) for a set of patients having early to moderate glaucoma (MD>−6 dB). The left graph shows the correlation between MD and RSCV and the right graph shows the correlation between NFL thickness and RSCV.

RSCV also showed good correlation with both visual field and NFL thickness in early and moderate glaucomatous eyes (FIG. 4), but retinal surface contour variability was not correlated with NFL in normal eyes (p=0.68).

TABLE 1

Diagnostic power of each structural parameter is evaluate by calculating the area under the receiver operating characteristic curve (AROC). SE is standard error.

|  | AROC ± SE | p-value (compared to RSCV) |
|---|---|---|
| RSCV (r = 3.0 mm) | 0.90 ± 0.05 | N/A |
| VRH (r = 3.0 mm) | 0.78 ± 0.08 | 0.10 |
| NFL Thickness (r = 1.7 mm) | 0.85 ± 0.06 | 0.42 |

In this preliminary study, an automatic algorithm was developed to calculate the RSCV, which characterizes the power in the identified spatial frequency range of ILM profiles. The RSCV metric demonstrated higher glaucoma diagnostic accuracy than vessel relief height and NFL thickness. Further, RSCV was correlated with functional visual field tests in subjects with diagnoses of early and moderate glaucoma. This method is the first to use the information contained in the ILM contour as segmented from OCT scans to assess NFL damage associated with glaucoma. The study described above is also the first to apply profile analysis using ILM contour to detect glaucoma.

Example 2

Second Pilot Study

Introduction

Glaucoma is a leading cause of blindness (Quigley H A et al, *Invest Ophthalmol Vis Sci* 38, 83-91 (1997); Hyman L et al, *Ophthalmology* 108, 1751-1756 (2001); incorporated by reference herein). Due to its insidious nature, an objective method to detect early glaucoma and glaucoma progression could help prevent vision loss and blindness. Optical coherence tomography (OCT) provides accurate and precise anatomical measurements of the optic nerve and retinal layers. Yet, its diagnostic sensitivities for detecting perimetric glaucoma (PG) are only 57-83% (Chang R T et al, *Ophthalmology* 116, 2294-2299(2009); Moreno-Montanes J et al, *Invest Ophthalmol Vis Sci* 51, 335-343(2010); Sung K R et al, *Ophthalmology* 116, 1264-1270, 1270 e1261(2009); Garas A et al, *Eur J Ophthalmol* 22, 45-54 (2012); Wu H et al, *Am J Ophthalmol* 153, 815-826 e812(2012); incorporated by reference herein) at a fixed specificity of 95%. In the Advanced Imaging for Glaucoma (AIG) study, at a 95% specificity set point, the sensitivity to detect PG was 100% for middle to late glaucoma stages (stages 3-5 on Glaucoma Staging System 2) (Brusini P and Filacorda S, *J Glaucoma* 15, 40-46 (2006); incorporated by reference herein). However, the sensitivity for early (stage 0-2) glaucoma was only 67%, still not sufficient for reliable early detection of glaucoma (Loewen N A et al, *Br J Ophthalmol* 99, 1224-1229 (2015); incorporated by reference herein). It has been estimated that about half of the glaucoma patients in the US do not know that they have the disease (Quigley H A et al, *Arch Ophthalmol* 119, 1819-1826 (2001); incorporated by reference herein). To tackle this public health problem, further improvement in objective diagnostic technology is needed.

Figure 5:
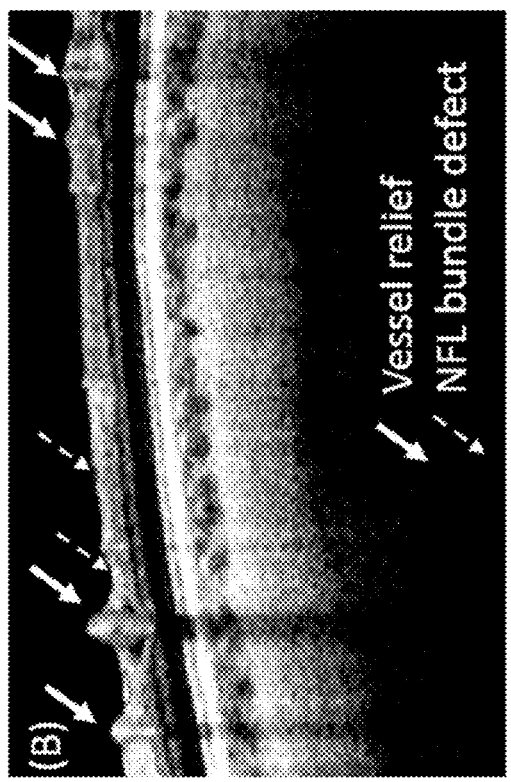
FIG. 5 is a panel of two exemplary images from the superior quadrant of cylindrical OCT cross sections of the peripapillary retina at 3 mm radius. (A) Normal (B) Glaucoma.
Figure 5:

Due to the high contrast between the retinal internal limiting membrane (ILM) and the overlying clear vitreous, the ILM can be delineated with high transverse resolution. This provides an excellent basis for detecting small scale, focal damage to the nerve fiber layer (NFL). Qualitatively, when studying the circumferential profile of the ILM around the optic nerve head, two types of change in glaucomatous eyes are visible (as shown in FIG. 5). First, there are focal depressions secondary to loss of nerve fiber bundles. Second, there are increased protrusions of retinal vessels above the plane of the NFL, presumably from loss of the NFL, which allows vessels to stand out in greater relief above the retinal plane. These focal depressions and vessel elevations will both increase the variations in height of the ILM profile. This novel parameter of focal NFL loss may be a sensitive indicator in early glaucoma, when total or average NFL loss is incomplete and variable.

In the pilot study described in this Example, a spatial frequency analysis method to measure the height variation in the ILM profile is developed, and its diagnostic power for detecting glaucoma is tested.

Methods

Participants:

The research protocol was approved by the institutional review board at the Oregon Health & Science University (OHSU) and carried out in accordance with the tenets of the Declaration of Helsinki. Written informed consent was obtained from each participant after explanation of the nature and possible consequences of the study. Participants were recruited at the Casey Eye Institute/OHSU according to the AIG study protocol. The OHSU ancillary site followed the same eligibility and endpoint protocol as the AIG study, but used an advanced swept-source OCT prototype system instead of commercially available OCT instruments. The inclusion and exclusion criteria of the AIG study were previously reported (Moreno-Montanes J et al, 2010 supra). Briefly, normal control participants met the following criteria in both eyes: intraocular pressures (IOP) of less than 21 mm Hg in both eyes, and a normal Humphrey visual field (HVF) on achromatic standard automated perimetry by Swedish Interactive Threshold Algorithm 24-2 testing (HFA II; Carl Zeiss Meditec, Inc., Dublin, Calif.) with mean deviation (MD), Glaucoma Hemifield Test (GHT), and pattern standard deviation (PSD) within normal limits. In addition, normal subjects had a normal appearing optic nerve head (ONH) and NFL on ophthalmoscopic examination, and an open angle by gonioscopy. Glaucoma participants were required to have a glaucomatous ONH rim or NFL thinning on ophthalmoscopic examination. Glaucomatous eyes were classified in the Perimetric Glaucoma (PG) subgroup if they have VF PSD or GHT outside normal limits ($P<0.05$ and $P<1\%$, respectively) in a consistent pattern on two qualifying VF exams. Otherwise, they were classified as Pre-Perimetric Glaucoma (PPG). Exclusion criteria for all groups included visual acuity less than 20/40, age <40 or >79 year at enrollment, any ocular surgery other than uncomplicated cataract extraction, other diseases that might cause VF or ONH abnormality, and factors that might preclude the participant from performing study procedures or completing the study.

OCT and Scanning:

A prototype high speed swept-source Fourier-domain OCT system was used in this study (Quigley H A et al, 2001 supra). The device operated at an axial scan speed of 100 kHz using a swept-source cavity laser operating at 1050 nm with a tuning range of 100 nm. A resolution of 5.3 µm axially and 18 µm laterally at an imaging depth of 2.9 mm in tissue was achieved. The ocular light power exposure was 1.9 mW, within the American National Standards Institute (ANSI) safety limit (ANSI Z136, New York (2007); incorporated by reference herein).

Participants were scanned using a high density 8×8 mm raster scan pattern, centered at the ONH. In the fast transverse scan direction, the B-scan consisted of 640 A-scans. The slow transverse scan direction included 640 B-scans. The time to acquire each 3D volumetric scan was 4.3 seconds. In the scan protocol, one eye of each participant was scanned with 4 scans consisting of 2 horizontal and 2 vertical scans. An orthogonal registration algorithm was applied to register and merge all 4 scans to reduce eye motion (Kraus M F et al, Biomed Opt Express 3, 1182-1199 (2012); incorporated by reference herein).

Figure 6:
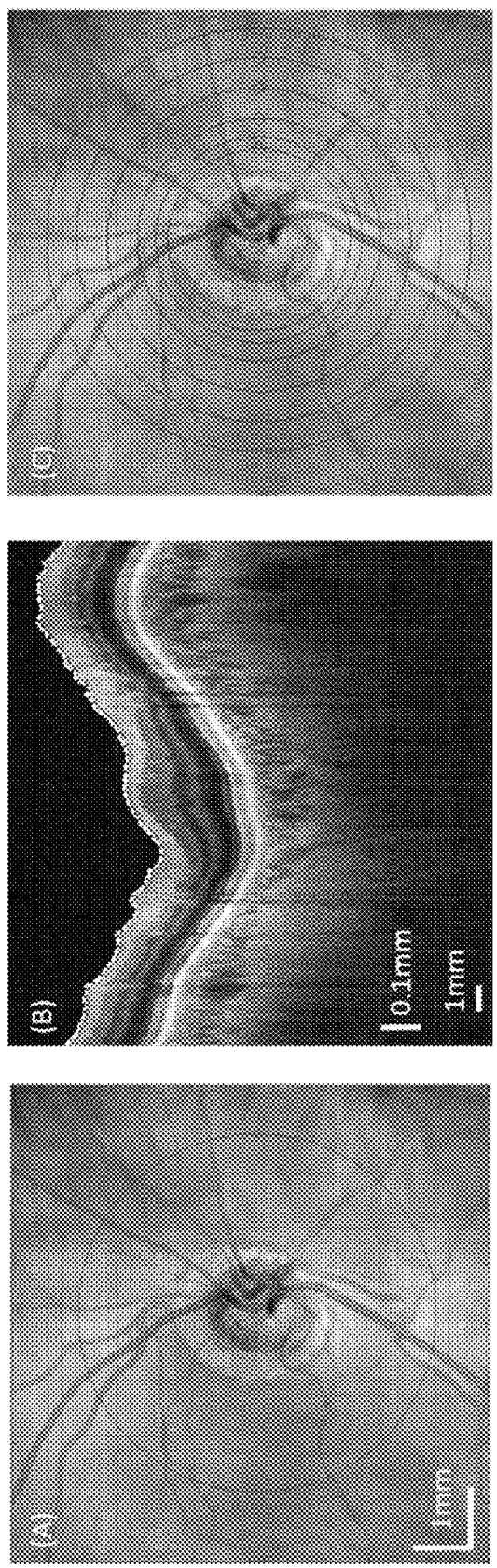
FIG. 6 is a panel of three images showing the cylindrical resampling scheme used to extract cross sectional data from a volumetric OCT scan. (A) En face view (average projection of log reflectance intensity) of the 8×8 mm volumetric "cube" scan of the optic nerve head (ONH) region in a glaucomatous eye. The 3 mm radius circle centered on the ONH is outlined in blue. (B) The 3-mm radius cylindrical cross section is resampled from the cube scan. The internal limiting membrane (ILM) contour (white dashed line) is measured from this circular cross section. (B) En face OCT showing resampling circles at radii of 1.5, 1.7, 2.0, 2.5, 3.0, and 3.5 mm.

Concentric, cylindrical, cross sectional OCT images of varying radii were resampled from the volume scan (FIG. 6) and upsampled to 1024 transverse points using interpolation. Rings were selected with radii of 1.5 mm, 1.7 mm, 2 mm, 2.5 mm, 3 mm and 3.5 mm for analysis.

ILM Detection:

The ILM was detected as the most inner boundary of retina in the cylindrical cross section images. An automated algorithm was developed to follow the vessel bumps and avoid artifacts, such as points of vitreous macular adhesion. The ILM elevation profile (contour) was extracted for each circle (FIG. 6B). Cross-sectional images with ILM contour overlay were inspected and manual correction of the contour was performed if necessary.

Retinal Surface Contour Variability:

The ILM elevation profile was transformed to spatial frequency domain using the fast Fourier transform (FIG. 7A). The spatial frequency components at lowest frequencies were removed because they simply relate to the average axial position and the tilt of the OCT scan beam relative to the ONH plane. The highest frequency components were also non-diagnostic because of high noise and minimal anatomic information. The middle frequency band that optimized the detection of retinal vessel relief and NFL bundle defects was determined empirically based on the difference between the average normal and glaucoma ILM spatial frequency spectrum (FIG. 7B). As shown for this particular population of participants, the middle frequency band that optimized detection had a range of approximately 5-100 radians/mm. The retinal surface contour variability (RSCV) was calculated as the average of frequency components in the optimized bands. These optimized bands were determined separately for each cylindrical section radius.

Nerve Fiber Layer Thickness:

On the cylindrical cross sectional OCT image with radius of 1.7 mm, the lower NFL boundary was also detected using a method previously described (Alasil T et al, *Ophthalmic Surg Lasers Imaging* 39, S71-79 (2008); incorporated by reference herein). The NFL thickness profile was defined as the distance between ILM and lower NFL boundary. The NFL thickness parameter was averaged along the profile.

Statistical Analysis:

The Wilcoxon rank sum test was performed to determine statistical significance between the study groups. The area under receiver operating characteristic curve (AROC) was calculated for the diagnostic accuracy. Pearson correlation was used to determine correlations between RSCV, NFL thickness, and visual field test MD. A coefficient of variance was applied to evaluate repeatability. All image processing and statistical analyses were done using Matlab software (The Mathworks, Natick, Mass.).

Results

Seventeen participants were enrolled in the glaucoma group: 8 in the PG subgroup and 9 in the PPG subgroup. Fifteen of them had early VF damage (MD>−6 dB) and 2 had more severe VF damage. Twenty-five participants were enrolled in the normal control group, but due to their younger average age, only the 17 oldest control participants were used in the present analysis. The age matching was not exact, as the control participants still averaged 9 years younger (Table 2). There were more females in the control group (Table 2). As expected, the glaucoma group had significantly worse VF MD and thinner NFL.

TABLE 2

Participant characteristics

|  | Normal | Glaucoma | p-value |
| --- | --- | --- | --- |
| Eye # | 17 | 17 | N/A |
| Age (years) | 59 ± 8 | 68 ± 8 | 0.11 |
| Female | 68% | 29% | 0.001 |
| Visual Field MD (dB) | 0.13 ± 0.79 | −2.48 ± 3.73 | 0.002 |
| NFL Thickness (μm) | 108.0 ± 9.9 | 88.6 ± 17.1 | 0.001 |

Figure 7:
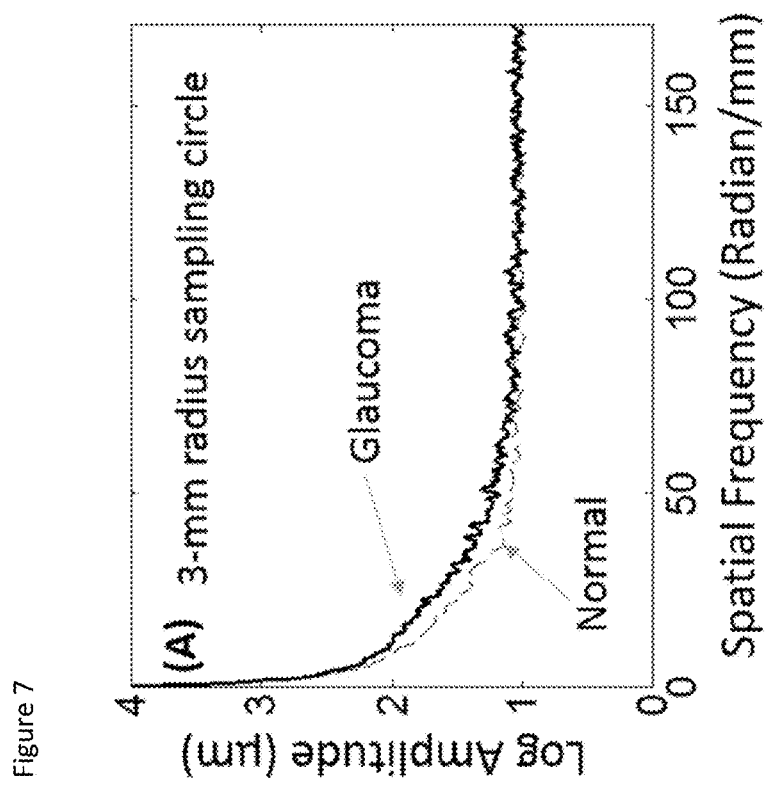
FIG. 7 is a panel of two graphs showing the spatial frequency content of a set of exemplary normal and glaucomatous eyes, plotted as log amplitude versus spatial frequency. (A) Spatial frequency spectrum of ILM elevation showing the averages of all glaucoma eyes and all normal eyes derived from the 3.0 mm OCT cylindrical sections. (B) shows the difference spectrum (glaucoma—normal) and the optimize frequency band (between blue dotted lines) used to compute the retinal surface contour variability (RSCV).
Figure 7:
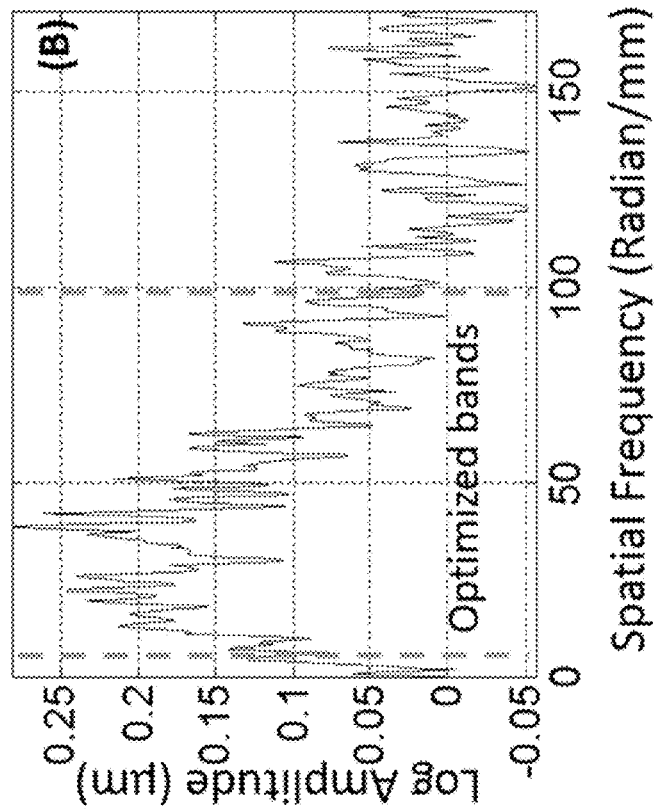
Figure 8:
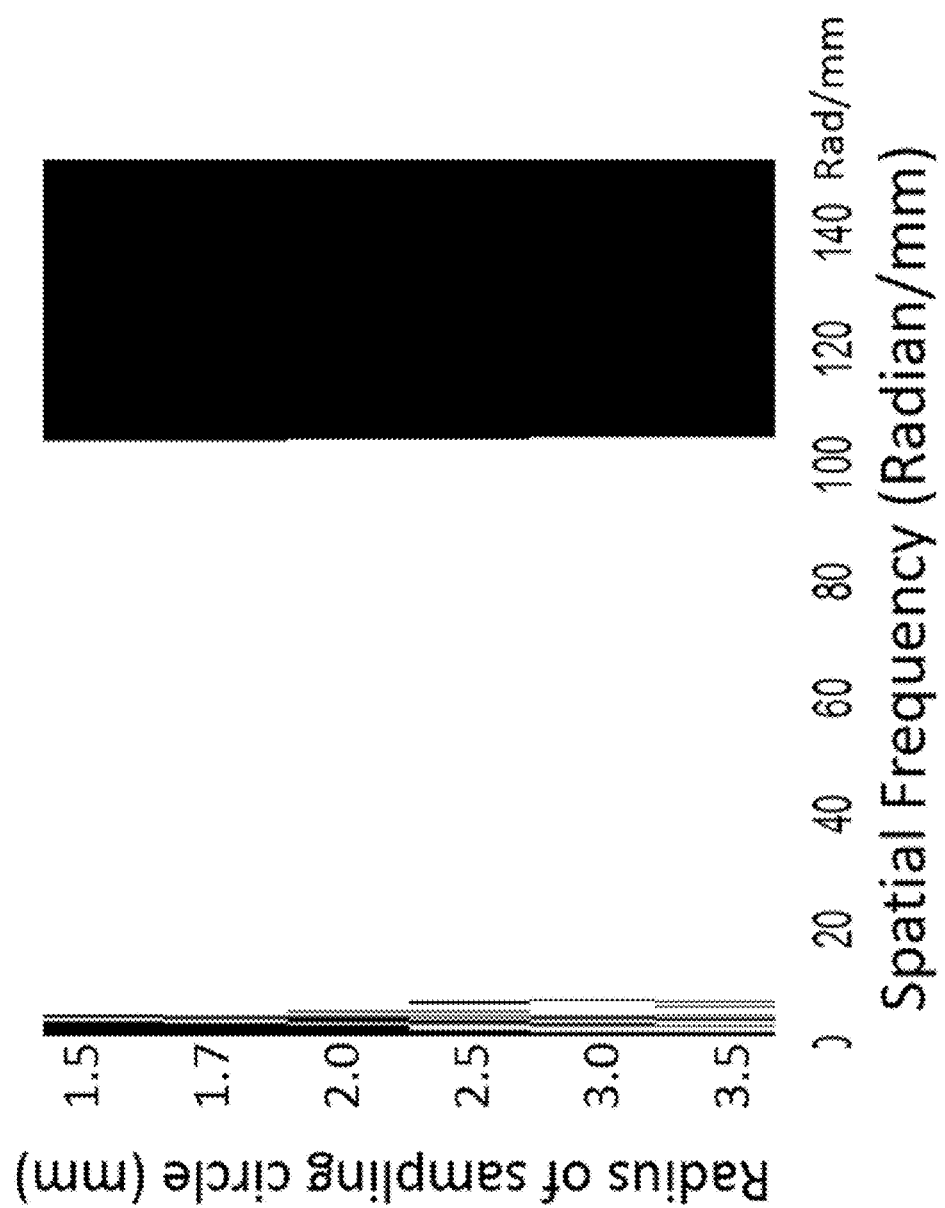
FIG. 8 is a graph showing the optimized spatial frequency passbands for RSCV calculation at different radii.
Figure 9:
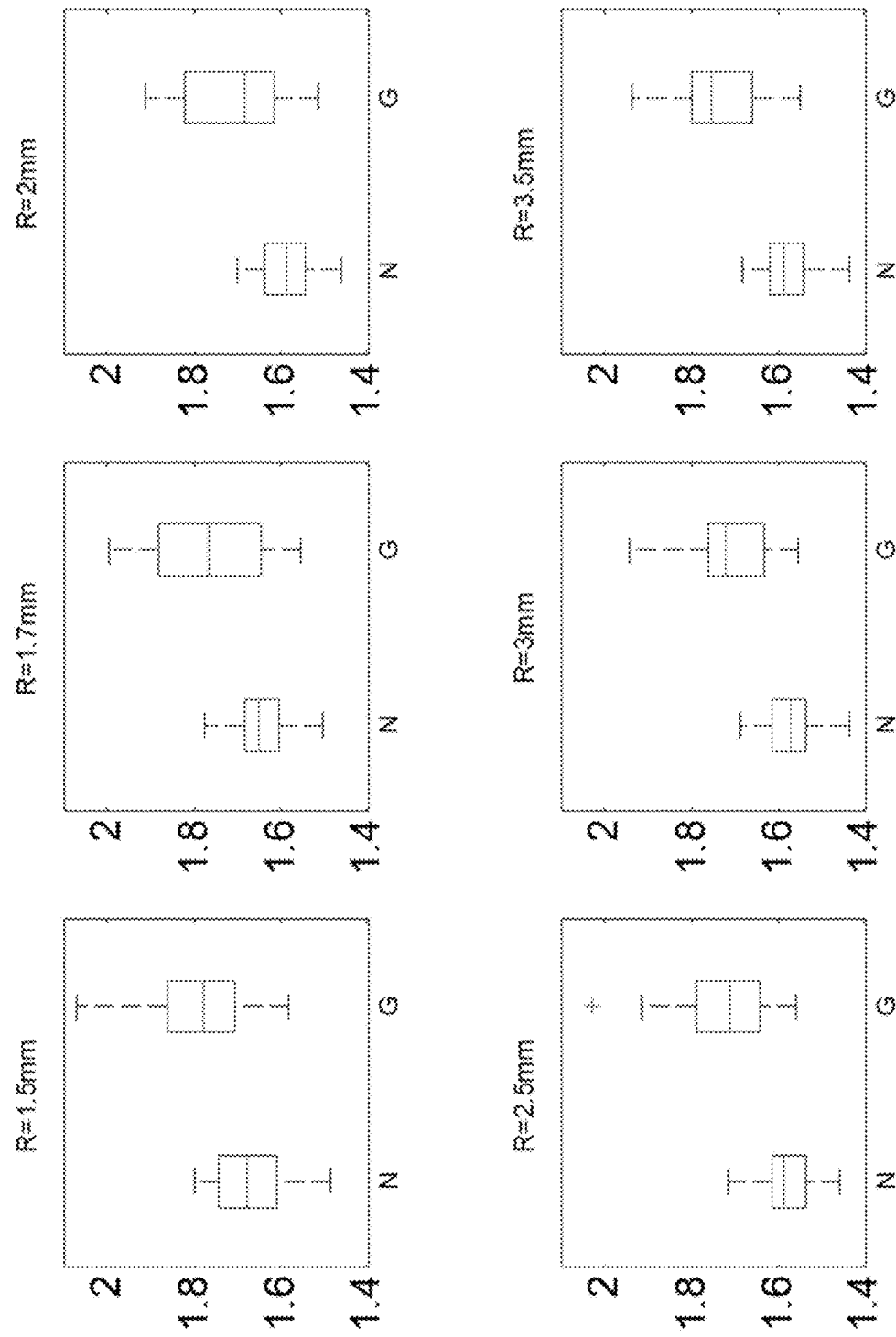
FIG. 9 is a panel of six graphs showing the distribution of RSVC values for normal (N) and glaucoma (G) groups at sampling radii between 1.5 mm and 3.5 mm.

The spatial frequency transforms of ILM profile were averaged for the normal and glaucoma groups (FIG. 7). Optimized bands were detected at frequency components where the glaucoma group was significantly larger than normal group (FIG. 8). RSCVs were averaged in the optimized bands for each circle and the RSCV distribution for normal and glaucoma groups are illustrated in FIG. 9. The RSCV was significantly higher at all sampling radii in the glaucoma group compared to the normal control group (Table 3).

TABLE 3

Retinal Surface Contour Variability as measured at different radii.

| Radius (mm) | Normal | Glaucoma | Difference |
| --- | --- | --- | --- |
| 3.5 | 1.58 ± 0.06 | 1.73 ± 0.10 | 0.15 |
| 3.0 | 1.57 ± 0.07 | 1.71 ± 0.10 | 0.14 |
| 2.5 | 1.58 ± 0.06 | 1.72 ± 0.13 | 0.14 |
| 2.0 | 1.59 ± 0.07 | 1.70 ± 0.12 | 0.11 |
| 1.7 | 1.64 ± 0.08 | 1.77 ± 0.13 | 0.13 |
| 1.5 | 1.67 ± 0.09 | 1.80 ± 0.13 | 0.13 |

Listed values are mean ± standard deviation of groups; all differences between the glaucoma and normal groups are significantly greater than zero ($p < 0.003$) by the Wilcoxon rand sum test.

The diagnostic accuracy of NFL and RSCV were assessed using AROC values at each sampling radius (Table 4). The diagnostic accuracy of RSCV improved with larger radii and the highest AROC value (0.90) was found at a radius of 3.5 mm. This was better than that for NFL thickness (0.84), but not significantly so (p=0.42). An examination of the averages of RSCV over various ranges of radii and found that the average over 2.5-3.5 mm had the highest AROC (0.91). When the averaged RSCV was combined with NFL using principal component analysis, the combination had marginally higher AROC (0.91) than NFL only (p=0.08).

TABLE 4

Diagnostic accuracy comparison.

| Parameter | Radius (mm) | AROC ± SE |
| --- | --- | --- |
| NFL Thickness | 1.58 ± 0.06 | 0.84 ± 0.07 |
| RSCV | 3.5 | 0.90 ± 0.05 |
|  | 3.0 | 0.87 ± 0.06 |
|  | 2.5 | 0.86 ± 0.06 |
|  | 2.0 | 0.78 ± 0.08 |
|  | 1.7 | 0.76 ± 0.09 |
|  | 1.5 | 0.77 ± 0.08 |
|  | 3.5 to 2.5 Average | 0.91 ± 0.05 |

Figure 10:
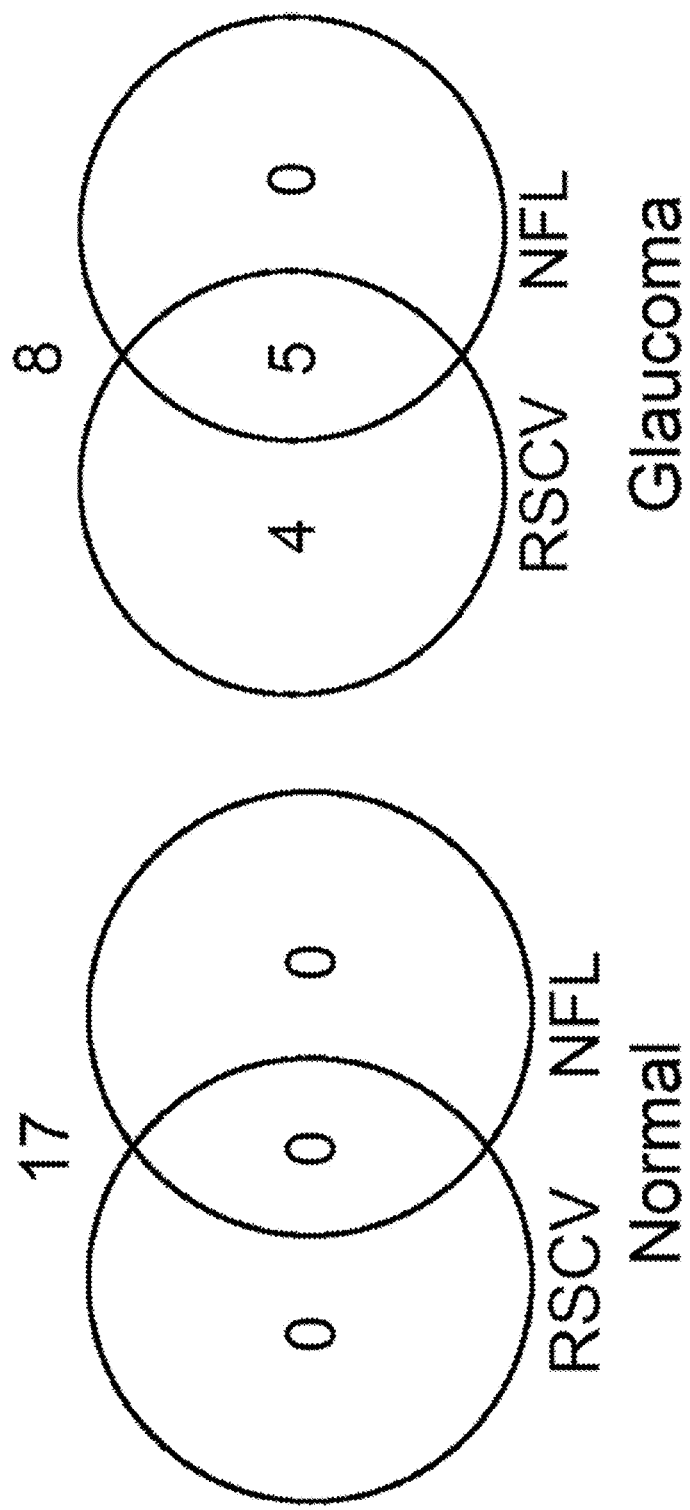
FIG. 10 is a Venn diagram for glaucoma diagnosis using both RSCV and NFL thickness parameters. The threshold for RSCV was set at 2.33 standard deviation (SD) above the mean of the normal group (99 percentile cutoff assuming normal distribution) and the threshold of NFL was 2.33 SD below the mean of normal group. In the normal group, all eyes were within the cutoff for both parameters, indicating 100% specificity. In the glaucoma groups, RSCV detected abnormality in 9 participants, including the 5 detected by NFL.

Venn diagram analysis (FIG. 10) showed that RSCV had higher sensitivity for glaucoma diagnosis (53%) than NFL thickness (29%). It was also notable that all abnormal eyes detected by NFL thickness were also detected by RSCV. However, the difference in sensitivity was not statistically significant (p=0.13). Both parameters had 100% specificity (FIG. 10).

The correlations between averaged RSCV and NFL thickness, or between averaged RSCV and VF MD, were estimated for glaucomatous participants (Table 5). Significant correlations were found between RSCV and NFL (r=−0.54, p=0.03) but not MD (R=−0.32, p=0.21). A significant correlation was also found between NFL and MD (r=0.68, p=0.002). The correlation between RSCV and NFL for normal participants were found to be not significant (r=−0.10, p=0.70).

TABLE 5

Correlation between glaucoma diagnostic parameters.

|  | RSCV (R = 2.5~3.5 mm) | NFL Thicknes (R = 1.7 mm) |
| --- | --- | --- |
| VF MD | r = 0.32, p = 0.21 | r = 0.68, p = 0.002 |
| NFL Thickness | r = 0.54, p = 0.03 | N/A |

It was also tested whether the RSCV was sensitive to transverse magnification changes (i.e. axial eye length variation) by comparing the values evaluated at the sampling radii of R=2.8 mm and 3 mm. No significant difference was found between the 2 radii in either the glaucoma or normal group (p>0.26). The coefficient of variation (CV) was 1.4% for normal eyes and 1.3% for glaucoma eyes. The between-grader reproducibility of RSCV was also tested because the ONH boundary and center were defined manually. The reproducibility (CV) was 1.6% for normal eyes and 1.1% for glaucoma eyes.

DISCUSSION

In this pilot study, spatial frequency analysis was used to detect small scale retinal surface contour change in glaucoma. The RSCV, when measured in the peripapillary area of the retina, was significantly larger in glaucoma eyes. The diagnostic accuracy of RSCV was at least as good as NFL thickness, but a larger study would be required to determine whether RSCV provides a significant diagnostic advantage. In early glaucoma, NFL thickness has limited diagnostic sensitivity, with literature values of 33.3%-67.4% at a fixed specificity of 99% (Chang R T et al, 2009 supra; Wu H et al, 2012 supra; Loewen N A et al, 2015 supra). This is expected due to the relatively wide range of population variation in the average NFL thickness, which has been reported as between 9.0% and 10.0% standard deviation (Sung K R et al, 2009 supra; Wu H et al, 2012 supra; Le P V et al, Am J Ophthalmol 159, 393-403 e392(2015); incorporated by reference herein). Because the RSCV measures small scale, focal changes that are unlikely to be due to the inborn variation of NFL thickness, it is better-suited to detect glaucoma in the earlier stages, when NFL damage is small and variable in location. In this pilot study, NFL thickness was abnormally (99% specificity cutoff) thin in only 5 out of 17 participants in the glaucoma group, while RSCV was abnormally elevated in 9 out of 17 glaucoma participants.

Because the NFL thickness and the RSCV measure different aspects of NFL damage—global versus focal—their combination may enhance diagnostic accuracy. While there is a previously developed parameter to measure focal peripapillary NFL and macular ganglion cell complex (GCC) thinning called focal loss volume (FLV), that algorithm was optimized to detect relatively larger areas (500 µm superpixels) of focal damage (Tan O et al, Ophthalmology 116, 2305-2314 e2301-2302 (2009); Tan O et al, Ophthalmology 115, 949-956 (2008); incorporated by reference herein). By contrast, the disclosed RSCV parameter is able to detect smaller focal changes. The RSCV spatial frequency analysis detects changes in the 2-100 radians/mm, which corresponds to spatial features as small as 60 µm (the diameter of a small arteriole) (Srinivas S et al, Invest Ophthalmol Vis Sci 56, 1569-1574 (2015); Hwang J C et al, Invest Ophthalmol Vis Sci 53, 3020-3026 (2012); incorporated by reference herein). Because these 3 parameters measure glaucoma damage on different spatial scales, they provide complementary information to aid diagnosis and may have synergistic explanatory power.

It was found that the RSCV appeared to have higher diagnostic accuracy in sampling circles with large radii (2.5-3.5 mm) compared to small radii (1.5-2 mm). There are at least two possible explanations for this observation. Firstly, the differences between normal and glaucoma group means were larger at the larger sampling radii. This might be due to the smaller RSCV values in the normal group at larger radii—the retinal surface becomes smoother further from the disc margin in normal eyes. This smoother normal reference makes detection of even small changes in the glaucomatous eyes more robust. This observation might be also due to the fact that glaucoma damages axon bundles non-uniformly within the ONH (laminar pores, etc) and these bundle losses may be more detectable within the NFL where all bundles are more spread out (i.e., more radially). Another assumption is that the thinner NFL away from the disc is going to be less likely to mask blood vessels and loss of axon bundles in these regions will reveal blood vessels in a more pronounced fashion. The second observation is that the population variances were tighter with larger radii (Table 3). This is likely due to the larger number of A-scans in sampling circles of larger radii. Thus, maximizing the OCT scan density in the 2.5-3.5 mm radius annulus around the optic disc may improve RSCV evaluation.

An additional advantage of RSCV over NFL thickness is that the RSCV value is relatively insensitive to magnification variation or decentration relative to the optic disc center. Between the scan radii of 2.5 to 3.5 mm, the mean RSCV values varied less than 2% in both normal and glaucoma groups. Inter-grader variation in disc boundary identification also affected RSCV by less than 2%. By comparison, NFL thickness does vary proportionately with magnification (axial eye length) (Sowmya V et al, J Clin Diagn Res 9, NC01-04 (2015); Savini G et al, Br J Ophthalmol 96, 57-61 (2012); Nagai-Kusuhara A et al, Br J Ophthalmol 92, 186-190 (2008); incorporated by reference herein). Furthermore, NFL quadrant thickness averages are known to be highly sensitive to decentration of the sampling circle relative to the optic disc (Campbell R J et al, Arch Ophthalmol 125, 624-627 (2007); Yoo C et al, Ophthalmologica 223, 326-332 (2009); incorporated by reference herein). Therefore, compared to NFL thickness, RSCV is a more robust diagnostic parameter that is relatively resistant to the introduction of bias due to patient factors, OCT operators, or graders.

In summary, the retinal surface contour variability was significantly increased in glaucoma eyes. The diagnostic accuracy of RSCV was at least equal to NFL thickness in early glaucoma. Since the RSCV detects small-scale focal damage and the average NFL thickness measures global damage, they provide different diagnostic information that is complementary and potentially synergistic.

Example 3

Figure 11:
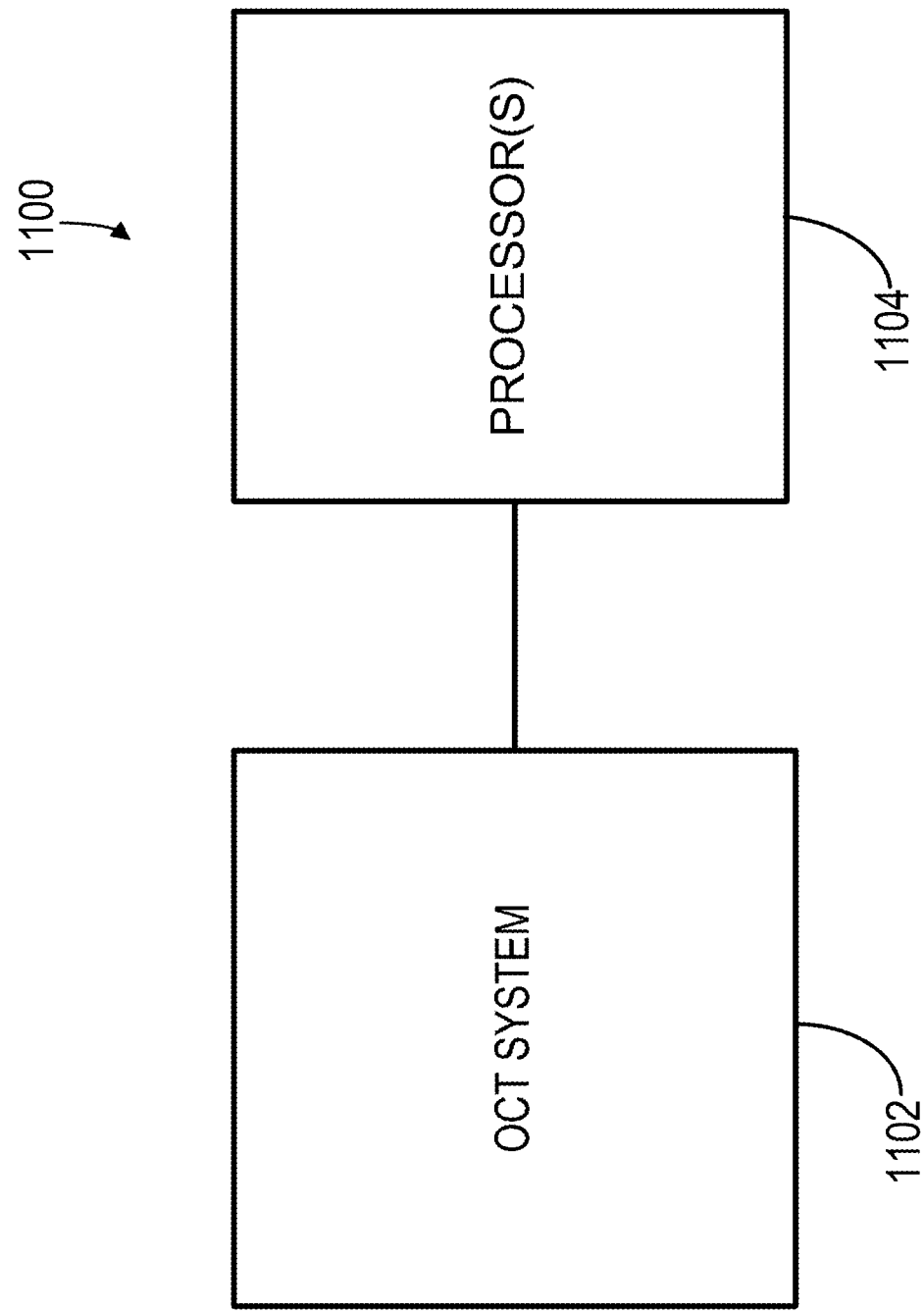
FIG. 11 is a schematic of an example system for processing OCT image data in accordance with the disclosure.

Optical Coherence Tomography Image Processing System for Glaucoma Detection FIG. 11 schematically shows an example system 1100 for OCT image processing in accordance with various embodiments. System 1100 comprises an OCT system 1102 configured to acquire an OCT image comprising OCT interferograms and one or more processors or computing systems 1104 that are configured to implement the various processing routines described herein. OCT system 1100 can comprise an OCT system suitable for structural OCT or OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods depicted in FIG. 3 described above, can be implemented as a computer application, computer service, computer API, computer library, and/or other computer program product.

Figure 12:
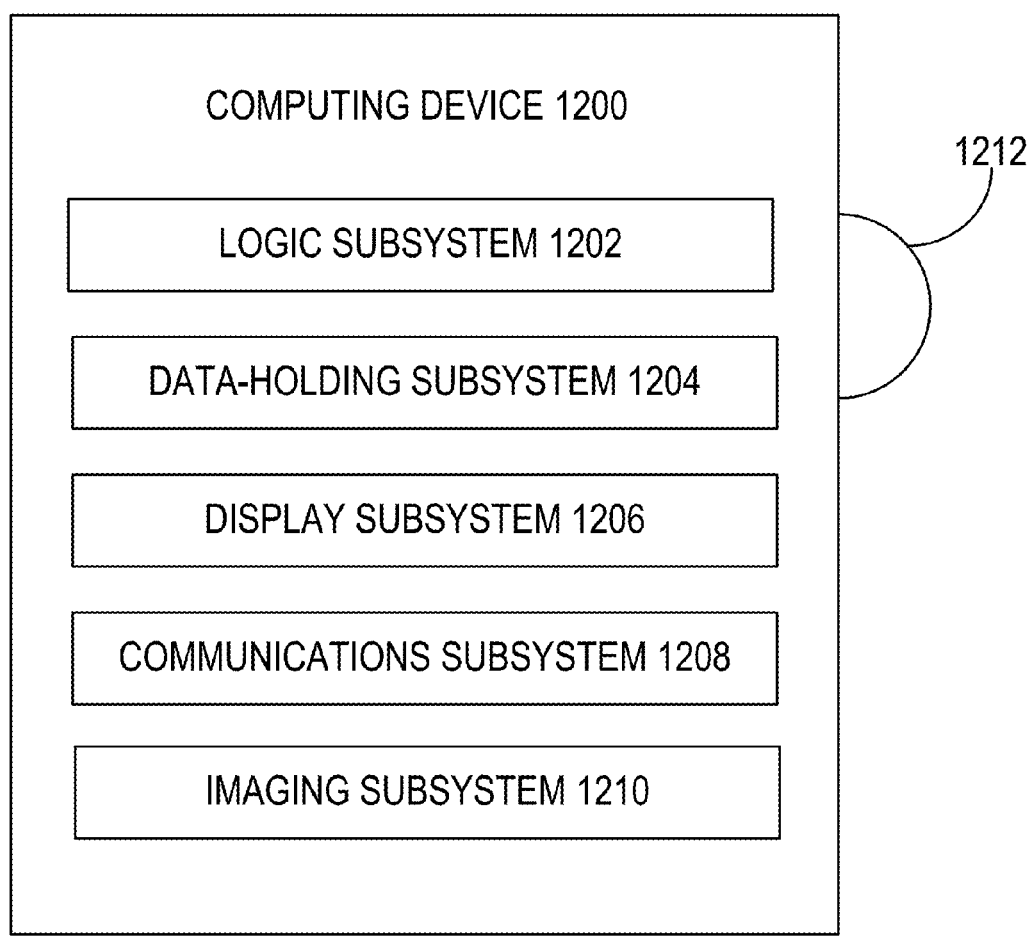
FIG. 12 is a schematic of an example computing system in accordance with the disclosure.

FIG. 12 schematically shows a non-limiting computing device 1200 that can perform one or more of the above described methods and processes. For example, computing device 1200 can represent a processor included in system 1100 described above, and can be operatively coupled to, in communication with, or included in an OCT system or OCT image acquisition apparatus. Computing device 1200 is shown in simplified form. It is to be understood that virtually any computer architecture can be used without departing from the scope of this disclosure. In different embodiments, computing device 1200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1200 includes a logic subsystem 1202 and a data-holding subsystem 1204. Computing device 1200 can optionally include a display subsystem 1206, a communication subsystem 1208, an imaging subsystem 1210, and/or other components not shown in FIG. 12. Computing device 1200 can also optionally include user input devices such as manually actuated buttons, switches, keyboards, mice, game controllers, cameras, microphones, and/or touch screens, for example.

Logic subsystem 1202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1204 can include one or more physical, non-transitory, devices configured to hold data and/or instructions executable by the logic subsystem to implement the herein described methods and processes. When such methods and processes are implemented, the state of data-holding subsystem 1204 can be transformed (e.g., to hold different data).

Data-holding subsystem 1204 can include removable media and/or built-in devices. Data-holding subsystem 1204 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1204 can include devices with one or more of the following characteristics: volatile, nonvolatile, dynamic, static, read/write, read-only, random access, sequential access, location addressable, file addressable, and content addressable. In some embodiments, logic subsystem 1202 and data-holding subsystem 1204 can be integrated into one or more common devices, such as an application specific integrated circuit or a system on a chip.

FIG. 12 also shows an aspect of the data-holding subsystem in the form of removable computer-readable storage media 1212, which can be used to store and/or transfer data and/or instructions executable to implement the herein described methods and processes. Removable computer-readable storage media 1212 can take the form of CDs, DVDs, HD-DVDs, Blu-Ray Discs, EEPROMs, flash memory cards, USB storage devices, and/or floppy disks, among others.

When included, display subsystem 1206 can be used to present a visual representation of data held by data-holding subsystem 1204. As the herein described methods and processes change the data held by the data-holding subsystem, and thus transform the state of the data-holding subsystem, the state of display subsystem 1206 can likewise be transformed to visually represent changes in the underlying data. Display subsystem 1206 can include one or more display devices utilizing virtually any type of technology. Such display devices can be combined with logic subsystem 1202 and/or data-holding subsystem 1204 in a shared enclosure, or such display devices can be peripheral display devices.

When included, communication subsystem 1208 can be configured to communicatively couple computing device 1200 with one or more other computing devices. Communication subsystem 1208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1200 to send and/or receive messages to and/or from other devices via a network such as the Internet.

When included, imaging subsystem 1210 can be used acquire and/or process any suitable image data from various sensors or imaging devices in communication with computing device 1200. For example, imaging subsystem 1210 can be configured to acquire OCT image data, e.g., interferograms, as part of an OCT system, e.g., OCT system 1102 described above. Imaging subsystem 1210 can be combined with logic subsystem 1202 and/or data-holding subsystem 1204 in a shared enclosure, or such imaging subsystems can comprise periphery imaging devices. Data received from the imaging subsystem can be held by data-holding subsystem 1204 and/or removable computer-readable storage media 1212, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of analyzing an optical coherence tomography (OCT) image of a region of an eye of a subject, the method comprising:
   receiving one or more transverse OCT images, said images depicting a cross sectional view of an inner limiting membrane (ILM) boundary of a retina;
   detecting the ILM boundary on the one or more transverse OCT images, thereby generating an ILM elevation profile;
   calculating a spatial frequency spectrum of the ILM elevation profile, the spatial frequency spectrum being comprised of a set of amplitudes;
   extracting a predetermined range of spatial frequency components from the spatial frequency spectrum;
   calculating a subject retinal surface contour variability (sRSCV) using the predetermined range of the spatial frequency components; and
   outputting an indication of a comparison between the sRSCV and an RSCV range.

2. The method of claim 1, wherein the indication comprises indicating the presence of an optic neuropathic disease condition.

3. The method of claim 2, wherein the optic neuropathic disease condition comprises a glaucoma condition.

4. The method of claim 1 wherein the transverse OCT images span a closed scan path approximately centered about the optic disc.

5. The method of claim 4 wherein the closed scan path is circular.

6. The method of claim 5 wherein the closed scan path has a radius of 1.5-3.5 mm.

7. The method of claim 1, wherein calculating the spatial frequency spectrum of the ILM elevation is performed using a Fourier transform.

8. The method of claim 1, wherein the predetermined range of spatial frequency components is comprised of one or more frequency ranges.

9. The method of claim 8, wherein the predetermined range of spatial frequency components comprises a low frequency range of approximately [0.2 cycle/mm to 0.3 cycle/mm] and a middle frequency range of approximately [0.7 cycle/mm to 13.2 cycle/mm].

10. The method of claim 8, wherein the predetermined range of spatial frequency components is approximately 5-100 radians/mm.

11. The method of claim 1, wherein calculating a subject retinal surface contour variability comprises calculating the average log amplitude of the frequency components in the predetermined range of spatial frequency components.

12. The method of claim 1 wherein the RSCV range is an RSCV normal range determined by calculating the RSCV for a set of subjects without the optic neuropathic disease and wherein an sRSCV that is outside the RSCV normal range signifies that the subject has the optic neuropathic disease.

13. The method of claim 12 further comprising determining the RSCV normal range.

14. The method of claim 1 wherein the RSCV range is an RSCV disease range determined by calculating the RSCV for a set of subjects with the optic neuropathic disease and wherein an sRSCV that is within the RSCV normal range signifies that the subject has the optic neuropathic disease.

15. The method of claim 14 further comprising determining the RSCV disease range.

* * * * *